United States Patent
Miller

(10) Patent No.: US 10,822,599 B2
(45) Date of Patent: *Nov. 3, 2020

(54) COMPOSITIONS FOR LINKING DNA-BINDING DOMAINS AND CLEAVAGE DOMAINS

(71) Applicant: Sangamo Therapeutics, Inc., Redmond, CA (US)

(72) Inventor: Jeffrey C. Miller, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 113 days.

This patent is subject to a terminal disclaimer.

(21) Appl. No.: 15/967,012

(22) Filed: Apr. 30, 2018

(65) Prior Publication Data

US 2018/0245058 A1 Aug. 30, 2018

Related U.S. Application Data

(60) Division of application No. 15/206,768, filed on Jul. 11, 2016, now Pat. No. 9,982,245, which is a continuation of application No. 12/455,143, filed on May 28, 2009, now Pat. No. 9,394,531.

(60) Provisional application No. 61/130,099, filed on May 28, 2008.

(51) Int. Cl.
   C07K 2/00 (2006.01)
   C12N 9/22 (2006.01)
   C12N 15/90 (2006.01)

(52) U.S. Cl.
   CPC ............. *C12N 9/22* (2013.01); *C12N 15/907* (2013.01); *C07K 2319/00* (2013.01); *C07K 2319/80* (2013.01)

(58) Field of Classification Search
   None
   See application file for complete search history.

(56) References Cited

U.S. PATENT DOCUMENTS

| | | |
|---|---|---|
| 5,356,802 A | 10/1994 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,534,261 B1 | 3/2003 | Cox, III et al. |
| 6,903,185 B2 | 6/2005 | Kim et al. |
| 7,153,949 B2 | 12/2006 | Kim et al. |
| 9,394,531 B2* | 7/2016 | Miller .................. C12N 15/907 |
| 9,982,245 B2* | 5/2018 | Miller .................. C12N 15/907 |
| 2005/0064474 A1 | 3/2005 | Urnov et al. |
| 2006/0063231 A1 | 3/2006 | Li et al. |
| 2006/0188987 A1 | 8/2006 | Guschin et al. |
| 2007/0134796 A1 | 6/2007 | Holmes et al. |
| 2008/0015164 A1 | 1/2008 | Collingwood |
| 2008/0131962 A1 | 6/2008 | Miller |
| 2009/0068164 A1 | 3/2009 | Segal et al. |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2005/014791 A2 | 2/2005 |
| WO | WO 07/014275 A2 | 2/2007 |
| WO | WO 2007/139898 A2 | 12/2007 |
| WO | WO 2007/139982 A2 | 12/2007 |
| WO | WO 2009/042163 A2 | 4/2009 |

OTHER PUBLICATIONS

Beerli, et al., "Engineering Polydactyl Zinc-Finger Transcription Factors," *Nature Biotechnology* 20:135-141 (2002).
Bibikova, et al., "Stimulation of Homologous Recombination Through Targeted Cleavage by Chimeric Nucleases," *Mol. Cell. Biol.* 21:289-297 (2001).
Bitinate, et al., "FokI Dimerization Is Required for DNA Cleavage," *PNAS USA* 95:10570-10575 (1998).
Choo, et al., "Advances in Zinc Finger Engineering," *Curr. Opin. Struct. Biol.* 10:411-416 (2000).
Händel, et al., "Expanding or Restricting the Target Site Repertoire of Zinc-Finger Nucleases: The Inter-Domain Linker As a Major Determinant of Target Site Selectivity," *Molecular Therapy* 17:104-111 (2009).
Isalan et al., "A Rapid, Generally Applicable Method to Engineer Zinc Fingers Illustrated by Targeting the HIV-1 Promoter," *Nat. Biotechnol.* 19:656-660 (2001).
Kim, et al., "Chimeric Restriction Endonuclease," *PNAS USA* 91:883-887 (1994).

(Continued)

Primary Examiner — Richard G Hutson
(74) Attorney, Agent, or Firm — Pasternak Patent Law

(57) ABSTRACT

Disclosed herein are compositions for linking DNA binding domains and cleavage domains (or cleavage half-domains) to form non-naturally occurring nucleases. Also described are methods of making and using compositions comprising these linkers.

5 Claims, 1 Drawing Sheet
Specification includes a Sequence Listing.

(56) References Cited

OTHER PUBLICATIONS

Kim, et al., "Hybrid Restriction Enzymes: Zinc Finger Fusions to Fok I Cleavage Domain," *PNAS USA* 93:1156-1160 (1996).
Kim, et al., "Insertion and Deletion Mutants of FokI Restriction Endonuclease," *J. Biol. Chem.* 269:31978-31981 (1994).
Lee, et al., "Rag Proteins Shepherd Double-Strand Breaks to a Specific Pathway Suppressing Error-Prone Repair, But Rag Nicking Initiates Homologous Recombination," *Cell* 117:171-184 (2004).
Li, et al., "Alteration of the Cleavage Distance of Fok I Restriction Endonuclease by Insertion Mutagenesis," *PNAS USA* 90:2764-2768 (1993).
Li, et al., "Functional Domains in Fok I Restriction Endonuclease," *PNAS USA* 89:4275-4279 (1992).
McConnell, et al., "Generation of a Nicking Enzyme That Stimulates Site-Specific Gene Conversion From the I-AniI Laglidadg Homing Endonuclease," *PNAS USA* 106(13):5099-5104 (2009).
Merutka, et al., "A Model Peptide With Enhanced Helicity," *Biochemistry* 30:4245-4248 (1991).
Miller, et al., "An Improved Zinc-Finger Nuclease Architecture for Highly Specific Genome Editing," *Nature Biotechnology* 25:778-785 (2007).
Miller, et al., "New Zinc Finger Protein Nuclease Architectures for More Efficient Gene Modification Therapies," *Molecular Therapy* 11:S147 (2005).
Pabo, et al., "Design and Selection of Novel CYS2-HIS2 Zinc Finger Proteins," *Ann. Rev. Biochem.* 70:313-340 (2001).
Roberts, et al., "Rebase: Restriction Enzymes and Methyltransferases," *Nucl. Acids. Res.* 31:418-420 (2003).
Sanders, et al., "Targeting Individual Subunits of the FokI Restriction Endonuclease to Specific DNA Strands," *Nucl. Acids. Res.* 37(7):2105-2115 (2009).
Segal, et al., "Custom DNA-Binding Proteins Come of Age: Polydactyl Zinc-Finger Proteins," *Curr. Opin. Biotechnol.* 12:632-637 (2001).
Smith et al., "Requirements for Double-Strand Cleavage by Chimeric Restriction Enzymes With Zinc Finger DNA-Recognition Domains," *Nucl. Acids. Res.* 28:3361-3369 (2000).
Szczepek, et al., "Structure-Based Redesign of the Dimerization Interface Reduces the Toxicity of Zinc-Finger Nucleases," *Nature Biotechnology* 25:786-793 (2007).
U.S. Appl. No. 61/205,970 for "Genomic Editing in Rats Using Zinc-Finnger Nucleases," filed Jan. 26, 2009 (Robins & Pasternak).
Wah, et al., "Structure of the Multimodular Endonuclease FokI Bound to DNA," *Nature* 388:97-100 (1997).
Yan, et al., "Alpha-Helical Linker of an Artificial 6-Zinc Finger Peptide Contributes to Selective DNA Binding to a Discontinuous Recognition Sequence," *Biochemistry* 46:8517-8524 (2007).

\* cited by examiner

FIGURE 1 (SEQ ID NO:1):

MDYKDHDGDYKDHDIDYKDDDDKMAPKKKRKVGIHGVPAA<u>MAERPFQCRIC
MRNFSDRSNLSRHIRTHTGEKPFACDICGRKFAISSNLNSHTKIHTGSQKPFQCRIC
MRNFSRSDNLARHIRTHTGEKPFACDICGRKFATSGNLTRHTKIHLRGS**QLVKSE
LEEKKS**</u>ELRHKLKYVPHEYIELIEIARNSTQDRILEMKVMEFFMKVYGYRGKHL
GGSRKPDGAIYTVGSPIDYGVIVDTKAYSGGYNLPIGQADEMQRYVEENQTRNK
HINPNEWWKVYPSSVTEFKFLFVSGHFKGNYKAQLTRLNHITNCNGAVLSVEEL
LIGGEMIKAGTLTLEEVRRKFNNGEINF

FIGURE 2 (SEQ ID NO:3):

MDYKDHDGDYKDHDIDYKDDDDKMAPKKKRKVGIHGVPAA<u>MAERPFQCRIC
MRNFSDRSNLSRHIRTHTGEKPFACDICGRKFAISSNLNSHTKIHTGSQKPFQCRIC
MRNFSRSDNLARHIRTHTGEKPFACDICGRKFATSGNLTRHTKIHLRGS**QLV*EAA
AR*ELEEKKS**</u>ELRHKLKYVPHEYIELIEIARNSTQDRILEMKVMEFFMKVYGYRG
KHLGGSRKPDGAIYTVGSPIDYGVIVDTKAYSGGYNLPIGQADEMQRYVEENQT
RNKHINPNEWWKVYPSSVTEFKFLFVSGHFKGNYKAQLTRLNHITNCNGAVLSV
EELLIGGEMIKAGTLTLEEVRRKFNNGEINF

FIGURE 3 (SEQ ID NO:4):

MDYKDHDGDYKDHDIDYKDDDDKMAPKKKRKVGIHGVPAA<u>MAERPFQCRIC
MRNFSDRSNLSRHIRTHTGEKPFACDICGRKFAISSNLNSHTKIHTGSQKPFQCRIC
MRNFSRSDNLARHIRTHTGEKPFACDICGRKFATSGNLTRHTKIHLRGS**QLVKS*K
SEAAAR*ELEEKK**</u>SELRHKLKYVPHEYIELIEIARNSTQDRILEMKVMEFFMKVYG
YRGKHLGGSRKPDGAIYTVGSPIDYGVIVDTKAYSGGYNLPIGQADEMQRYVEE
NQTRNKHINPNEWWKVYPSSVTEFKFLFVSGHFKGNYKAQLTRLNHITNCNGA
VLSVEELLIGGEMIKAGTLTLEEVRRKFNNGEINF

COMPOSITIONS FOR LINKING DNA-BINDING DOMAINS AND CLEAVAGE DOMAINS

CROSS-REFERENCE TO RELATED APPLICATIONS

The present application is a divisional of U.S. patent application Ser. No. 15/206,768, filed Jul. 11, 2016, which is a continuation of U.S. patent application Ser. No. 12/455,143, filed May 28, 2009, now U.S. Pat. No. 9,394,531, which claims the benefit of U.S. Provisional Application No. 61/130,099, filed May 28, 2008. The disclosures of all the foregoing applications are hereby incorporated by reference in their entireties.

STATEMENT OF RIGHTS TO INVENTIONS MADE UNDER FEDERALLY SPONSORED RESEARCH

Not applicable.

TECHNICAL FIELD

The present disclosure is in the fields of genome and protein engineering.

BACKGROUND

Artificial nucleases comprising DNA binding domains operably linked to cleavage domains have been used for targeted alteration of genomic sequences. For example, zinc finger nucleases have been used to insert exogenous sequences, inactivate one or more endogenous genes, create organisms (e.g., crops) and cell lines with altered gene expression patterns, and the like. See, e.g., U.S. Patent Publication Nos. 2005/0064474; 2006/0063231; 2007/0134796; 2008/0015164 and International Patent Publication No. 2007/139982.

A pair of zinc finger nucleases is typically used to cleave genomic sequences. Each member of the pair generally includes an engineered (non-naturally occurring) zinc finger protein linked to one or more cleavage domains (or half-domains) of a nuclease. When the zinc finger proteins bind to their target sites, the cleavage domains that are linked to those zinc finger proteins are positioned such that dimerization and subsequent cleavage of the genome can occur, generally between the pair of the zinc finger nucleases.

It has been shown that cleavage activity of the ZFN pair is related to both the length of the linker joining the zinc finger and the cleavage domain ("ZC" linker) and the distance between the target sites (binding sites). See, for example, Smith, et al. (2000) Nucleic Acids Res. 28:3361-3369; Bibikova, et al. (2001) Mol. Cell. Biol. 21:289-297. When using pairs of zinc finger nuclease fusion proteins (ZFNs), optimal cleavage with currently available ZC linkers and cleavage half domains has been obtained when the binding sites for the fusion proteins are located 5 or 6 nucleotides apart (as measured from the near edge of each binding site). See, e.g., U.S. Patent Publication No. 2005/0064474.

Thus, there remains a need for methods and compositions that allow targeted modification where the artificial nucleases can cleave endogenous genomic sequences with binding site separations other than 5 bp or 6 bp. The ability to target sequences with different spacings would increase the number of genomic targets that can be cleaved. Altering the preferences between target sites separated by different numbers of basepairs could also allow the artificial nucleases to act with greater specificity.

SUMMARY

Disclosed herein are compositions for linking DNA-binding domains and cleavage domains to form nucleases, for example nucleases with altered target site separation (gap) preferences as compared to conventional linkers. Also described are fusion proteins comprising these linkers. The disclosure also provides methods of using these fusion proteins and compositions thereof for targeted cleavage of cellular chromatin in a region of interest and/or homologous recombination at a predetermined region of interest in cells.

Thus, in one aspect, the linkers described herein comprise a conventional ZC linker and, in addition, include sequences that alter the N-terminal region of the cleavage domains. In certain embodiments, the alterations include additions or substitutions in the N-terminal region, for example to form an N-terminal sequence that adopts a stable alpha helical conformation and/or extends the alpha helical conformation of the wild-type cleavage domain. Thus, alteration of the N-terminal region may include addition, substitution and/or deletion of wild-type residues, for example deletion of wild-type residues in the N-terminal region of a FokI cleavage half-domain and insertion of additional residues. In certain embodiments, the cleavage domain includes 3 or 5 additional amino acids in the cleavage domain as compared to wild-type, for example cleavage domain N-terminal regions comprising EXXXR (SEQ ID NO:9) or EXXXK (SEQ ID NO:10), wherein X is any amino acid residue except proline or glycine. In certain embodiments, the alterations to the N-terminus of the cleavage domain are those shown in FIG. 2 or 3. In certain embodiments, the alteration to the N-terminal region is such that an alpha helix is formed in the N-terminal region of the cleavage domain. Unlike previously disclosed cleavage domains incorporated into ZFNs that dimerize to cleave DNA sequences separated 5 or 6 basepairs, the cleavage domains of the present disclosure allow for targeted cleavage when the target sites of the pair of ZFNs are not 5 or 6 base pairs apart.

In any of the embodiments in which the cleavage domain is generated by altering the N-terminal region, the wild-type alpha-helical region of the cleavage domain may be unaltered. Furthermore, the altered N-terminal regions can be designed to form helices that may extend the N-terminal most helix in the wild-type cleavage domain (e.g., addition of EXXXR (SEQ ID NO:9) or EXXXK (SEQ ID NO:10) N-terminal to the ELEEKKSELRHK (SEQ ID NO: 7) sequence of a wild-type FokI cleavage domain). In another aspect, fusion polypeptides comprising a zinc finger binding domain (e.g., an engineered zinc finger binding domain), a cleavage half-domain and a linker as described herein are provided.

In another aspect, polynucleotides encoding any of the linkers or fusion proteins as described herein are provided.

In yet another aspect, cells comprising any of the polypeptides (e.g., fusion polypeptides) and/or polynucleotides as described herein are also provided. In one embodiment, the cells comprise a pair of fusion polypeptides, each comprising a cleavage domain as disclosed herein.

In yet another aspect, methods for targeted cleavage of cellular chromatin in a region of interest; methods of causing homologous recombination to occur in a cell; methods of treating infection; and/or methods of treating disease are provided. The methods involve cleaving cellular chromatin at a predetermined region of interest in cells by expressing a pair of fusion polypeptides, at least one of which comprises a linker (e.g., ZC linker and altered cleavage domain) as described herein. In certain embodiments, one fusion polypeptide comprises a linker (e.g., ZC linker and altered N-terminal region of a cleavage domain) as described herein and in other embodiments, both fusion polypeptides comprise a linker (e.g., ZC linker and altered N-terminal region of a cleavage domain) as described herein. Furthermore, in any of the methods described herein, the pair of fusion polypeptides cleave the targeted region when the binding sites for the zinc finger nucleases are 3, 4, 5, 6, 7, 8, 9 or even more base pairs apart.

The polypeptides comprising the linkers as described herein can be used in methods for targeted cleavage of cellular chromatin in a region of interest and/or homologous recombination at a predetermined region of interest in cells. Cells include cultured cells, cells in an organism and cells that have been removed from an organism for treatment in cases where the cells and/or their descendants will be returned to the organism after treatment. A region of interest in cellular chromatin can be, for example, a genomic sequence or portion thereof.

A fusion protein can be expressed in a cell, e.g., by delivering the fusion protein to the cell or by delivering a polynucleotide encoding the fusion protein to a cell, wherein the polynucleotide, if DNA, is transcribed, and an RNA molecule delivered to the cell or a transcript of a DNA molecule delivered to the cell is translated, to generate the fusion protein. Methods for polynucleotide and polypeptide delivery to cells are presented elsewhere in this disclosure.

Accordingly, in another aspect, a method for cleaving cellular chromatin in a region of interest can comprise (a) selecting a first sequence in the region of interest; (b) engineering a first zinc finger binding domain to bind to the first sequence; (c) expressing a first fusion protein in the cell, the first fusion protein comprising the first zinc finger binding domain, a cleavage half-domain; and (d) expressing a second fusion protein in the cell, the second fusion protein comprising a second zinc finger binding domain, a second cleavage half-domain, wherein at least one of the fusion proteins comprises a linker (e.g., ZC linker and altered N-terminal region of a cleavage domain) as described herein, and further wherein the first fusion protein binds to the first sequence, and the second fusion protein binds to a second sequence located between 2 and 50 nucleotides from the first sequence, such that cellular chromatin is cleaved in the region of interest. In certain embodiments, both fusion proteins comprise a linker (e.g., ZC linker and altered N-terminal region of a cleavage domain) as described herein.

In other embodiments, the disclosure provides methods of cleaving cellular chromatin by (a) selecting first and second sequences in a region of interest, wherein the first and second sequences are between 2 and 50 nucleotides apart; (b) engineering a first zinc finger binding domain to bind to the first sequence; (c) engineering a second zinc finger binding domain to bind to the second sequence; (d) expressing a first fusion protein in the cell, the first fusion protein comprising the first engineered zinc finger binding domain, a first ZC linker, and a first cleavage half domain as described herein; (e) expressing a second fusion protein in the cell, the second fusion protein comprising the second engineered zinc finger binding domain, a second ZC linker and a second cleavage half-domain; wherein the first fusion protein binds to the first sequence and the second fusion protein binds to the second sequence, thereby cleaving the cellular chromatin in the region of interest. In certain embodiments, the second fusion protein also comprises a cleavage half domain as described herein.

In further embodiments, a method for cleavage of cellular chromatin in a region of interest comprises (a) selecting the region of interest; (b) engineering a first zinc finger binding domain to bind to a first sequence in the region of interest; (c) providing a second zinc finger binding domain which binds to a second sequence in the region of interest, wherein the second sequence is located between 2 and 50 nucleotides from the first sequence; (d) expressing a first fusion protein in the cell, the first fusion protein comprising the first zinc finger binding domain, a first ZC linker and a first cleavage half-domain as described herein; and (e) expressing a second fusion protein in the cell, the second fusion protein comprising the second zinc finger binding domain, a second ZC linker and a second cleavage half domain; wherein the first fusion protein binds to the first sequence, and the second fusion protein binds to the second sequence, thereby cleaving the cellular chromatin in the region of interest. In certain embodiments, the second fusion protein comprises a cleavage half domain as described herein.

Also provided are methods of altering a region of cellular chromatin, for example to introduce targeted mutations. In certain embodiments, methods of altering cellular chromatin comprise introducing into the cell one or more targeted nucleases to create a double-stranded break in cellular chromatin at a predetermined site, and a donor polynucleotide, having homology to the nucleotide sequence of the cellular chromatin in the region of the break. Cellular DNA repair processes are activated by the presence of the double-stranded break and the donor polynucleotide is used as a template for repair of the break, resulting in the introduction of all or part of the nucleotide sequence of the donor into the cellular chromatin. Thus, a sequence in cellular chromatin can be altered and, in certain embodiments, can be converted into a sequence present in a donor polynucleotide.

Targeted alterations include, but are not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations.

The donor polynucleotide can be DNA or RNA, can be linear or circular, and can be single-stranded or double-stranded. It can be delivered to the cell as naked nucleic acid, as a complex with one or more delivery agents (e.g., liposomes, poloxamers) or contained in a viral delivery vehicle, such as, for example, an adenovirus or an adeno-associated Virus (AAV). Donor sequences can range in length from 10 to 1,000 nucleotides (or any integral value of nucleotides therebetween) or longer.

In certain embodiments, the frequency of homologous recombination can be enhanced by arresting the cells in the G2 phase of the cell cycle and/or by activating the expression of one or more molecules (protein, RNA) involved in homologous recombination and/or by inhibiting the expression or activity of proteins involved in non-homologous end-joining.

In any of the methods described herein, the first and second zinc finger proteins of the fusion proteins can bind to target sites 2, 3, 4, 5, 6, 7, 8 or 9 base pairs apart. In addition, in any of the methods, the second zinc finger binding domain may be engineered to bind to the second sequence.

Furthermore, in any of the methods described herein, the fusion proteins may be encoded by a single polynucleotide.

For any of the aforementioned methods, the cellular chromatin can be in a chromosome, episome or organellar genome. Cellular chromatin can be present in any type of cell including, but not limited to, prokaryotic and eukaryotic cells, fungal cells, plant cells, animal cells, mammalian cells, primate cells and human cells.

In another aspect, described herein is a kit comprising a linker (e.g., ZC linker and altered N-terminal region of a cleavage domain) as described herein or a polynucleotide encoding a linker (e.g., ZC linker and altered N-terminal region of a cleavage domain) as described herein; ancillary reagents; and optionally instructions and suitable containers. The kit may also include one or more nucleases or polynucleotides encoding such nucleases.

In any of the proteins, methods and kits described herein, the cleavage domain (or cleavage half-domain) may comprise a TypeIIS cleavage domain, such as a cleavage half-domain from FokI.

These and other aspects will be readily apparent to the skilled artisan in light of disclosure as a whole.

BRIEF DESCRIPTION OF THE DRAWINGS

FIG. 1 depicts the sequence of an exemplary zinc finger nuclease that binds to a target site in CCR5 (SEQ ID NO:1). The zinc finger domain is doubly underlined. The entire FokI cleavage domain is underlined and the N-terminal region is underlined and bolded. The "ZC" linker (LRGS; SEQ ID NO:2) is shown in plain text between the zinc finger and cleavage domains.

FIG. 2 depicts the sequence of an exemplary zinc finger nuclease as described herein including a linker designated "L6a" (SEQ ID NO:3). The zinc finger domain is doubly underlined. The entire FokI cleavage domain is underlined and the N-terminal region, including alterations as compared to wild-type, is underlined and bolded. The amino acids differing from wild-type are shown in italics (EAAAR; SEQ ID NO:5). The "ZC" linker (LRGS; SEQ ID NO:2) is shown in plain text between the zinc finger and cleavage domains.

FIG. 3 depicts the sequence of another exemplary zinc finger nuclease as described herein including a linker designated "L7a" (SEQ ID NO:4). The zinc finger domain is doubly underlined. The entire FokI cleavage domain is underlined and the N-terminal region, including alterations as compared to wild-type, is underlined and bolded. The amino acids different from wild-type are shown in italics (KSEAAAR; SEQ ID NO:6). The "ZC" linker (LRGS; SEQ ID NO:2) is shown in plain text between the zinc finger and cleavage domains.

DETAILED DESCRIPTION

Described herein are compositions for linking DNA-binding domains and cleavage domains to form artificial nucleases and methods of using these nucleases for targeted alteration of a cellular nucleotide sequence, e.g., by targeted cleavage followed by non-homologous end joining; by targeted cleavage followed by homologous recombination between an exogenous polynucleotide (comprising one or more regions of homology with the cellular nucleotide sequence) and a genomic sequence; by targeted inactivation of one or more endogenous genes.

Exemplary linkers as shown FIGS. 2 and 3 include alterations to the N-terminal region of the cleavage domain. The alterations increase the ability of a pair of ZFNs to cleave when the ZFN target sites are more (or less) than 5 or 6 base pairs apart. Thus, certain linkers described herein significantly increase the ability to perform targeted genomic alteration by increasing the cleavage activity when the zinc finger target sites are not separated by 5 or 6 base pairs.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also International Patent Publication No. WO 98/53058; WO 98/53059; WO 98/53060; WO 02/016536; and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; and 6,200,759; International Patent Publication Nos. WO 95/19431; WO 96/06166; WO 98/53057; WO 98/54311; WO 00/27878; WO 01/60970; WO 01/88197; and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication No. 2005/0064474 and International Patent Publication No. WO 2007/13989, incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule, a malfunctioning version of a normally-functioning endogenous molecule or an ortholog (functioning version of endogenous molecule from a different species).

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Gene inactivation refers to any reduction in gene expression as compared to a cell that does not include a ZFP as described herein. Thus, gene inactivation may be partial or complete.

"Eukaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields, et al. (1989) Nature 340:245-246; U.S. Pat. No. 5,585,245 and International Patent Publication No. WO 98/44350.

Linkers

Described herein are amino acid sequences that fuse (link) a DNA binding domain (e.g., zinc finger protein) and a nuclease (e.g., a cleavage domain or cleavage half-domain).

Currently, when a pair of zinc finger nucleases is used to cleave a genomic sequence, optimal cleavage is obtained when the zinc finger proteins bind to target sites separated by 5-6 base pairs and a flexible "ZC" linker rich in glycine and serine is used to join each zinc finger of the pair to the cleavage domain. In particular, the "ZC" linker used to date consists of the amino acid sequence LRGS (SEQ ID NO:2) between the C-terminal of the zinc finger binding domain and the N-terminal residues of the cleavage domain, which in the case of FokI is a Q residue. See, e.g., U.S. Patent Publication No. 2005/0064474 and International Patent Publication No. WO 07/139898.

The linkers described herein are more rigid than the linkers previously used, and allow cleavage when the target sites of a pair of zinc finger nucleases are not 5-6 base pairs apart. The linker sequences may be created by adding additional residues to the "ZC" linker, for example by adding amino acid residues (1, 2, 3, 4, 5, 6, 7, 8, 9, 10 or even more) to the linker sequence N-terminal to the first residue (Q) of the cleavage domain. It will be apparent that the number of residues added between the zinc finger and cleavage domains will in some measure depend on amino acid alterations made to the cleavage domain. For example, if residues are deleted from the N-terminal region of the cleavage domain, additional residues may be added to between the zinc finger and cleavage domains. Alternatively, if residues are added within the N-terminal region of the cleavage domain (e.g., C-terminal to the first residue (Q) of a FokI cleavage domain), a ZC linker (or other 4 residue sequence) may be used between the zinc finger protein and cleavage domain.

The linkers described herein may also be generated by altering the N-terminal region of the selected cleavage domain. Alteration may include substitutions, additions and/or deletions of one or more N-terminal residues of the cleavage domain. In certain embodiments, the cleavage domain is derived from FokI and one or more amino acids of the wild-type FokI N-terminal region are replaced and additional amino acids added to this region. For example, as shown in FIG. 2, amino acid residues 4 and 5 of the wild-type FokI cleavage domain (i.e., residues K and S) are replaced with residues E and A, respectively and the residues AAR is added C-terminal to the $2^{nd}$ replaced residue. Another exemplary embodiment (FIG. 3) includes a seven residue insertion (KSEAAAR; SEQ ID NO:6) in the N-terminal region of the FokI cleavage domain.

The sequence joining the DNA-binding domain and the cleavage domain can comprise any amino acid sequence that does not substantially hinder the ability of the DNA-binding domain to bind to its target site or the cleavage domain to dimerize and/or cleave the genomic sequences. In wild-type FokI, the N-terminal region of the cleavage domain includes an alpha helical region extending from residues 389-400 (ELEEKKSELRHK; SEQ ID NO:7). See, e.g., Wah, et al. (1997) Nature 388:97-100). Therefore, in certain embodiments, the linker sequences are designed to extend and/or conserve this structural motif, for example by inserting a 3-5 amino sequence N-terminal to ELEEKKSELRHK of a wild-type FokI cleavage domain.

Thus, the linker may include a sequence such as EXXXR (SEQ ID NO:9) or EXXXK (SEQ ID NO:10) where the X residues are any residues that form an alpha helix, namely any residue except proline or glycine (e.g., EAAAR (SEQ ID NO:8)) adjacent to the wild-type alpha helical region to form a stable alpha helix linker. See, e.g., Yan, et al. (2007) *Biochemistry* 46:8517-24 and Merutka and Stellwagen (1991) Biochemistry 30:4245-8. Placing an EXXXR (SEQ ID NO:9) or EXXXK (SEQ ID NO:10) peptide adjacent (or near to) to the ELEEKKSELRHK (SEQ ID NO: 7) peptide is designed to extend this alpha helix in FokI cleavage domain. This creates a more rigid linker between the ZFP and FokI cleavage domain which allows the resulting ZFN pair to cleave a target with more than 6 bp between the half sites without the loss in activity and specificity that can be observed when a long flexible linker is used between the ZFP and the FokI domain (Bibikova, et al. (2001) Molecular and Cellular Biology 21:289-297). In addition, the linkers described herein show a greater preference for a 6 bp spacing over a 5 bp spacing as compared to current ZFNs.—Typically, the linkers of the invention are made by making recombinant nucleic acids encoding the linker and the DNA-binding domains, which are fused via the linker amino acid sequence. Optionally, the linkers can also be made using peptide synthesis, and then linked to the polypeptide DNA-binding domains.

Nucleases

The linker sequences described herein are advantageously used to link DNA-binding domains, for example zinc finger proteins, to nuclease cleavage domains or half domains to form specifically targeted, non-naturally occurring nucleases.

A. DNA-Binding Domains

Any DNA-binding domain can be used in the methods disclosed herein. In certain embodiments, the DNA binding domain comprises a zinc finger protein. Preferably, the zinc finger protein is non-naturally occurring in that it is engineered to bind to a target site of choice. See, for example, Beerli, et al. (2002) *Nature Biotechnol.* 20:135-141; Pabo, et al. (2001) *Ann. Rev. Biochem.* 70:313-340; Isalan, et al. (2001) *Nature Biotechnol.* 19:656-660; Segal, et al. (2001) *Curr. Opin. Biotechnol.* 12:632-637; Choo, et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in co-owned International Patent Publication No. WO 02/077227.

Selection of target sites; ZFPs and methods for design and construction of fusion proteins (and polynucleotides encoding same) are known to those of skill in the art and described in detail in U.S. Patent Publication Nos. 2005/0064474 and 2006/0188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort, et al. (1997) *Nucleic Acids Res.* 25:3379-3388; Dujon et al. (1989) *Gene* 82:115-118; Perler, et al. (1994) *Nucleic Acids Res.* 22, 1125-1127; Jasin (1996) *Trends Genet.* 12:224-228; Gimble, et al. (1996)*J Mol. Biol.* 263:163-180; Argast, et al. (1998)*J Mol. Biol.* 280:345-353 and the New England Biolabs catalogue. In addition, the DNA-binding specificity of homing endonucleases and meganucleases can be engineered to bind non-natural target sites. See, for example, Chevalier, et al. (2002) *Molec. Cell* 10:895-905; Epinat, et al. (2003) *Nucleic Acids Res.* 31:2952-2962; Ashworth, et al. (2006) *Nature* 441:656-659; Paques, et al. (2007) *Current Gene Therapy* 7:49-66; U.S. Patent Publication No. 2007/0117128.

B. Cleavage Domains

The nucleases described herein (e.g., ZFNs) also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort, et al. (1997) *Nucleic Acids Res.* 25:3379-3388. Additional enzymes which cleave DNA are known (e.g., Si Nuclease; mung bean nuclease; pancreatic DNase I; micrococcal nuclease; yeast HO endonuclease; see also Linn, et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof).

In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150; and 5,487,994; as well as Li, et al. (1992) *Proc. Natl. Acad. Sci. USA* 89:4275-4279; Li, et al. (1993) *Proc. Natl. Acad. Sci. USA* 90:2764-2768; Kim, et al. (1994a) *Proc. Natl. Acad. Sci. USA* 91:883-887; Kim, et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite, et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts, et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 2005/0064474 and 2006/0188987 and in U.S. Patent Publication No. US-2008-0131962-A1, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., Example 1 of International Patent Publication No. WO 07/139898.

Engineered cleavage half-domains described herein can be prepared using any suitable method, for example, by site-directed mutagenesis of wild-type cleavage half-domains (Fok I) as described in U.S. Patent Publication No. 2005/0064474 (see, e.g., Example 5); and International Patent Publication No. WO 07/139898.

Alternatively, nucleases may be assembled in vivo at the nucleic acid target site using so-called "split-enzyme" technology (see e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Kits

Also provided are kits comprising any of the linkers described herein and/or for performing any of the above methods. The kits typically contain a linker sequence as described herein (or a polynucleotide encoding a linker as described herein). The kit may supply the linker alone or may provide vectors into which a DNA-binding domain and/or nuclease of choice can be readily inserted into. The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

Applications

The disclosed linkers are advantageously used in combination with zinc finger proteins to cleave DNA, for example when the target sites of a pair of zinc finger proteins used for cleavage are not 5 or 6 base pairs apart. Cleavage can be at a region of interest in cellular chromatin (e.g., at a desired or predetermined site in a genome, for example, in a gene, either mutant or wild-type); to replace a genomic sequence (e.g., a region of interest in cellular chromatin) with a homologous non-identical sequence (i.e., targeted recombination); to delete a genomic sequence by cleaving DNA at one or more sites in the genome, which cleavage sites are then joined by non-homologous end joining (NHEJ); to screen for cellular factors that facilitate homologous recombination; and/or to replace a wild-type sequence with a mutant sequence, or to convert one allele to a different allele. Such methods are described in detail, for example, in U.S. Patent Publication No. 2005/0064474; International Patent Publication No. WO 07/014275, incorporated by reference in their entireties herein.

Accordingly, the disclosed linkers can be used in any ZFN for any method in which specifically targeted cleavage is desirable and/or to replace any genomic sequence with a homologous, non-identical sequence. For example, a mutant genomic sequence can be replaced by its wild-type counterpart, thereby providing methods for treatment of e.g., genetic disease, inherited disorders, cancer, and autoimmune disease. In like fashion, one allele of a gene can be replaced by a different allele using the methods of targeted recombination disclosed herein. Indeed, any pathology dependent upon a particular genomic sequence, in any fashion, can be corrected or alleviated using the methods and compositions disclosed herein.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6$^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. See, International Patent Publication WO 2007/139982. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4.

ZFNs containing the disclosed linkers can also be used for inactivation (partial or complete) of one or more genomic sequences. Inactivation can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause missplicing of the transcript.

ZFN-mediated inactivation (e.g., knockout) of endogenous genes can be used, for example, to generate cell lines deficient in genes involved in apoptosis or protein production (e.g., post-translational modifications such as fucosylation). ZFN-mediated inactivation can also be used to generate transgenic organisms (e.g., plants, rodents and rabbits).

In addition, because ZFNs don't appear to have specificity for the DNA sequence between the two half sites, ZFNs with linkers as described herein can be designed to cleave DNA such that the resulting single-stranded overhangs have any desired sequence. In particular, linkers as described herein can be designed to influence both the size and position of these single-stranded overhangs with respect to the starting sequence. Thus, when incorporated into ZFNs, linkers as described herein can result in more uniform ends following cleavage. Accordingly, the linkers described herein can also be used to more efficiently clone DNA cut with ZFNs, which is broadly applicable in many areas of biotechnology and basic science.

Thus, the linkers described herein provide broad utility for improving ZFN-mediated cleavage in gene modification applications. Linkers as described herein may be readily incorporated into any existing ZFN by either site directed mutagenesis or subcloning to be used in many applications in standard cloning, constructing large genomes for synthetic biology, new types of RFLP analysis of large sequences or even allow new types of cloning involving extremely large DNA sequences. The potential properties of ZFNs with rigid linkers could also be ideal in applications such as DNA computing.

EXAMPLES

Example 1: Design and Construction of ZFNs with Rigid Linkers

Zinc finger nuclease constructs targeted to the human CCR5 locus were prepared as disclosed in International Patent Publication No. WO 2007/139982. Wild-type constructs included the "ZC" linker. The ZFN construct with the rigid linker designed "L6a" is shown in FIG. 2. The construct with a rigid linker designated "L7a" is shown in FIG. 3.

In addition, pairs of ZFNs targeted to sequences in the human mitochondria containing the mutation that causes MELAS (mitochondrial myopathy, encephalopathy, lactic acidosis, and stroke) were also prepared to include the L7a linker.

Example 2: ZFN Activity

A. CCR5-Targeted ZFNs

Constructs encoding CCR5-targeted ZFN SBS #8266 were initially tested in a yeast Mel-I reporter system as described in WO 2009/042163. In particular, yeast strains having an inverted repeat of the SBS #8266 target site separated by 3, 4, 5, 6, 7, or 8 bp were used to characterize the constructs.

The wild-type ZFN (with the standard LRGSQLVK-SELEEKKS linker) (SEQ ID NO: 11) showed strong activity with 5 bp and 6 bp half site spacings. In addition, the constructs with the L6a linker sequence (FIG. 2) showed activity at 6p spacings and the L7a linker sequence (FIG. 3) showed significant activity with 7 bp and 8 bp spacings. In vitro DNA binding and cleavage activity of the MELAS-targeted ZFNs was also assayed and pairs of ZFNs including the rigid L7a linker cleaved their target.

Finally, the CCR5 ZFNs including the L7a linker were tested for NHEJ activity at the endogenous human CCR5 locus in cell lines that contain various numbers of basepairs between the half sites. Results are shown in Table 1.

TABLE 1

| ZFN | target sites separated by | % NHEJ (exp't #1) | % NHEJ (exp't #2) | % NHEJ (average) |
|---|---|---|---|---|
| Wt ZFNs | 4 bp | 1.2 | 1.1 | 1.2 |
| Wt ZFNs | 5 bp | 36.0 | 34.0 | 35.0 |
| Wt ZFNs | 6 bp | 13.4 | 8.8 | 11.1 |
| Wt ZFNs | 7 bp | 0.0 | 0.0 | 0.0 |
| Wt ZFNs | 8 bp | 0.0 | 0.0 | 0.0 |
| L6a ZFNs | 4 bp | 0.0 | 0.0 | 0.0 |
| L6a ZFNs | 5 bp | 44.4 | 34.1 | 39.3 |
| L6a ZFNs | 6 bp | 26.2 | 24.6 | 25.4 |
| L6a ZFNs | 7 bp | 6.5 | 3.7 | 5.1 |
| L6a ZFNs | 8 bp | 0.0 | 0.0 | 0.0 |
| L7a ZFNs | 4 bp | 0.0 | 0.0 | 0.0 |
| L7a ZFNs | 5 bp | 0.0 | 0.0 | 0.0 |
| L7a ZFNs | 6 bp | 33.1 | 30.5 | 31.8 |
| L7a ZFNs | 7 bp | 41.1 | 38.1 | 39.6 |
| L7a ZFNs | 8 bp | 7.9 | 4.6 | 6.1 |

As expected, the wild-type ZFNs only showed high activity at half-sites separated by 5 or 6 bp. However, CCR5-targeted ZFNs including the rigid L7a linker showed high activity with a 7 bp spacing and noticeable activity with the 8 bp spacing. It should be noted that the efficiency of the L7a constructs with the 7 bp spacing is very similar to the efficiency of the wild type ZFNs with a 5 bp spacing (either in the wild-type cell line or a cell line with a different sequence of the 5 bp in between the half sites).

In addition, combinations of linkers were also tested in CCR5-targeted ZFN pairs. Briefly, K562 cells were engineered to have gaps of 4 to 8 base pairs (bp) between the CCR5 ZFN binding sites. Two CCR5 ZFNs with different linkers combinations (Wt/L7a) were transfected into these K562 cells by Amaxa Shuttle. Samples were harvested 3 days after transfection and subjected to CEL1-I assay analysis. CEL-I mismatch assays were performed essentially as per the manufacturer's instructions (Trangenomic SURVEYOR™).

The results indicate that the Wt/Wt linker ZFN has the highest activity with 5 bp gap target sequence; the L7a/L7a linker ZFN had the highest activity with a 7 bp gap sequence, and the ZFNs with Wt/L7a or L7a/Wt linker combinations had the highest activity with a 6 bp gap sequence.

B. ROSA-Targeted ZFNs

Neuro2A cells were transfected with combinations of mROSA-targeted ZFNs (see, e.g., U.S. Patent Publication No. 2007/0134796) by Amaxa Shuttle using a target site with a 6 bp gap. One ZFN of the pairs included a wild-type linker ("ZC") and the other included either wild-type or L7a linker as described herein. Samples were harvested 3 days after transfection and subjected to CEL-I analysis, as described above and in U.S. Patent Publication No. 2007/0134796.

As shown in Table 2 below, the wild type (WT)/L7a linker in a pair of ZFNs is active with a 6 bp gap.

TABLE 2

| Sample | Linker #1 | Linker #2 | % NHEJ |
|---|---|---|---|
| mock transfection (no ZFN) | NA | NA | 0.4 |
| Rosa-ZFN pairs | Wt | Wt | 22.6 |
| Rosa-ZFN pairs | Wt | L7a | 7.5 |
| Rosa-ZFN pairs | Wt | Wt | 23.2 |
| Rosa-ZFN pairs | Wt | Wt | 18.7 |
| GFP-ZFN pairs | Wt | L7a | 5.3 |
| GFP-ZFN pairs | Wt | Wt | 21.5 |

C. Rat IgM

Rat C6 cells were transfected with combinations of rat IgM-targeted ZFNs (see, e.g., U.S. Patent Application No. 61/205,970) by Amaxa Shuttle using a target site with a 6 bp gap. One ZFN of the pairs included a wild-type linker ("ZC") and the other included either wild-type or L7a linker as described herein. Samples were harvested 9 days after transfection and subjected to CEL-I analysis, as described above and in U.S. Patent Publication No. 2007/0134796.

Cells containing the pair of ZFNs that included the L7a linkers showed 2.43% NHEJ as compared to cells containing a pair of ZFNs that included the ZC linker, which showed 1.93% NHEJ. Furthermore, the L7a-containing linker ZFN pair was used to inject into rat ES cells (as described in U.S. Patent Application No. 61/205,970) and these ES cells successfully produced homozygous IgM gene knockout rat offspring.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A polynucleotide encoding a nuclease comprising:
   a DNA-binding domain that binds to a nucleotide target site; and
   a FokI cleavage domain, wherein the FokI cleavage domain comprises a substitution of amino acid residues 161 and 162 of SEQ ID NO:1 with an amino acid sequence EAAAR (SEQ ID NO:5) or an insertion after amino acid residue 162 of SEQ ID NO:1 of an amino acid sequence KSEAAAR (SEQ ID NO:6).

2. The polynucleotide of claim 1, wherein the nucleotide target site is an endogenous gene.

3. A cell comprising the polynucleotide according to claim 1.

4. A kit for producing a nuclease, the kit comprising the polynucleotide according to claim 1 contained in one or more containers, optional hardware, and instructions for use of the kit.

5. The kit of claim 4, further comprising a donor polynucleotide.

* * * * *

SEQUENCE LISTING

<160> NUMBER OF SEQ ID NOS: 11

<210> SEQ ID NO 1
<211> LENGTH: 353
<212> TYPE: PRT
<213> ORGANISM: Artificial Sequence
<220> FEATURE:
<223> OTHER INFORMATION: Synthetic zinc finger nuclease

<400> SEQUENCE: 1

Met Asp Tyr Lys Asp His Asp Gly Asp Tyr Lys Asp His Asp Ile Asp
1               5                   10                  15

-continued

Tyr Lys Asp Asp Asp Lys Met Ala Pro Lys Lys Arg Lys Val
            20                  25                  30

Gly Ile His Gly Val Pro Ala Ala Met Ala Glu Arg Pro Phe Gln Cys
            35                  40                  45

Arg Ile Cys Met Arg Asn Phe Ser Asp Arg Ser Asn Leu Ser Arg His
50                  55                  60

Ile Arg Thr His Thr Gly Glu Lys Pro Phe Ala Cys Asp Ile Cys Gly
65                  70                  75                  80

Arg Lys Phe Ala Ile Ser Ser Asn Leu Asn Ser His Thr Lys Ile His
                85                  90                  95

Thr Gly Ser Gln Lys Pro Phe Gln Cys Arg Ile Cys Met Arg Asn Phe
            100                 105                 110

Ser Arg Ser Asp Asn Leu Ala Arg His Ile Arg Thr His Thr Gly Glu
            115                 120                 125

Lys Pro Phe Ala Cys Asp Ile Cys Gly Arg Lys Phe Ala Thr Ser Gly
            130                 135                 140

Asn Leu Thr Arg His Thr Lys Ile His Leu Arg Gly Ser Gln Leu Val
145                 150                 155                 160

Lys Ser Glu Leu Glu Glu Lys Lys Ser Glu Leu Arg His Lys Leu Lys
                165                 170                 175

Tyr Val Pro His Glu Tyr Ile Glu Leu Ile Glu Ile Ala Arg Asn Ser
            180                 185                 190

Thr Gln Asp Arg Ile Leu Glu Met Lys Val Met Glu Phe Phe Met Lys
            195                 200                 205

Val Tyr Gly Tyr Arg Gly Lys His Leu Gly Gly Ser Arg Lys Pro Asp
210                 215                 220

Gly Ala Ile Tyr Thr Val Gly Ser Pro Ile Asp Tyr Gly Val Ile Val
225                 230                 235                 240

Asp Thr Lys Ala Tyr Ser Gly Gly Tyr Asn Leu Pro Ile Gly Gln Ala
                245                 250                 255

Asp Glu Met Gln Arg Tyr Val Glu Glu Asn Gln Thr Arg Asn Lys His
            260                 265                 270

Ile Asn Pro Asn Glu Trp Trp Lys Val Tyr Pro Ser Ser Val Thr Glu
            275                 280                 285

Phe Lys Phe Leu Phe Val Ser Gly His Phe Lys Gly Asn Tyr Lys Ala
290                 295                 300

Gln Leu Thr Arg Leu Asn His Ile Thr Asn Cys Asn Gly Ala Val Leu
305                 310                 315                 320

Ser Val Glu Glu Leu Leu Ile Gly Gly Glu Met Ile Lys Ala Gly Thr
                325                 330                 335

Leu Thr Leu Glu Glu Val Arg Arg Lys Phe Asn Asn Gly Glu Ile Asn
            340                 345                 350

Phe

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Leu Arg Gly Ser
1

```
<210> SEQ ID NO 3
<211> LENGTH: 356
<212> TYPE: PRT
<213> ORGANISM: Artificial Sequence
<220> FEATURE:
<223> OTHER INFORMATION: Synthetic zinc finger nuclease

<400> SEQUENCE: 3

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Ile His Gly Val Pro Ala Ala Met Ala Glu Arg Pro Phe Gln Cys
            35                  40                  45

Arg Ile Cys Met Arg Asn Phe Ser Asp Arg Ser Asn Leu Ser Arg His
        50                  55                  60

Ile Arg Thr His Thr Gly Glu Lys Pro Phe Ala Cys Asp Ile Cys Gly
65                  70                  75                  80

Arg Lys Phe Ala Ile Ser Ser Asn Leu Asn Ser His Thr Lys Ile His
                85                  90                  95

Thr Gly Ser Gln Lys Pro Phe Gln Cys Arg Ile Cys Met Arg Asn Phe
            100                 105                 110

Ser Arg Ser Asp Asn Leu Ala Arg His Ile Arg Thr His Thr Gly Glu
        115                 120                 125

Lys Pro Phe Ala Cys Asp Ile Cys Gly Arg Lys Phe Ala Thr Ser Gly
    130                 135                 140

Asn Leu Thr Arg His Thr Lys Ile His Leu Arg Gly Ser Gln Leu Val
145                 150                 155                 160

Glu Ala Ala Ala Arg Glu Leu Glu Glu Lys Lys Ser Glu Leu Arg His
                165                 170                 175

Lys Leu Lys Tyr Val Pro His Glu Tyr Ile Glu Leu Ile Glu Ile Ala
            180                 185                 190

Arg Asn Ser Thr Gln Asp Arg Ile Leu Glu Met Lys Val Met Glu Phe
        195                 200                 205

Phe Met Lys Val Tyr Gly Tyr Arg Gly Lys His Leu Gly Gly Ser Arg
    210                 215                 220

Lys Pro Asp Gly Ala Ile Tyr Thr Val Gly Ser Pro Ile Asp Tyr Gly
225                 230                 235                 240

Val Ile Val Asp Thr Lys Ala Tyr Ser Gly Tyr Asn Leu Pro Ile
                245                 250                 255

Gly Gln Ala Asp Glu Met Gln Arg Tyr Val Glu Glu Asn Gln Thr Arg
            260                 265                 270

Asn Lys His Ile Asn Pro Asn Glu Trp Trp Lys Val Tyr Pro Ser Ser
        275                 280                 285

Val Thr Glu Phe Lys Phe Leu Phe Val Ser Gly His Phe Lys Gly Asn
    290                 295                 300

Tyr Lys Ala Gln Leu Thr Arg Leu Asn His Ile Thr Asn Cys Asn Gly
305                 310                 315                 320

Ala Val Leu Ser Val Glu Glu Leu Leu Ile Gly Gly Glu Met Ile Lys
                325                 330                 335

Ala Gly Thr Leu Thr Leu Glu Glu Val Arg Arg Lys Phe Asn Asn Gly
            340                 345                 350

Glu Ile Asn Phe
            355
```

```
<210> SEQ ID NO 4
<211> LENGTH: 360
<212> TYPE: PRT
<213> ORGANISM: Artificial Sequence
<220> FEATURE:
<223> OTHER INFORMATION: Synthetic zinc finger nuclease

<400> SEQUENCE: 4
```

| Met | Asp | Tyr | Lys | Asp | His | Asp | Gly | Asp | Tyr | Lys | Asp | His | Asp | Ile | Asp |
|---|---|---|---|---|---|---|---|---|---|---|---|---|---|---|---|
| 1 | | | | 5 | | | | | 10 | | | | | 15 | |

Tyr Lys Asp Asp Asp Lys Met Ala Pro Lys Lys Arg Lys Val
                20                  25                  30

Gly Ile His Gly Val Pro Ala Ala Met Ala Glu Arg Pro Phe Gln Cys
            35                  40                  45

Arg Ile Cys Met Arg Asn Phe Ser Asp Arg Ser Asn Leu Ser Arg His
50                  55                  60

Ile Arg Thr His Thr Gly Glu Lys Pro Phe Ala Cys Asp Ile Cys Gly
65                  70                  75                  80

Arg Lys Phe Ala Ile Ser Ser Asn Leu Asn Ser His Thr Lys Ile His
                85                  90                  95

Thr Gly Ser Gln Lys Pro Phe Gln Cys Arg Ile Cys Met Arg Asn Phe
            100                 105                 110

Ser Arg Ser Asp Asn Leu Ala Arg His Ile Arg Thr His Thr Gly Glu
        115                 120                 125

Lys Pro Phe Ala Cys Asp Ile Cys Gly Arg Lys Phe Ala Thr Ser Gly
    130                 135                 140

Asn Leu Thr Arg His Thr Lys Ile His Leu Arg Gly Ser Gln Leu Val
145                 150                 155                 160

Lys Ser Lys Ser Glu Ala Ala Ala Arg Glu Leu Glu Glu Lys Lys Ser
                165                 170                 175

Glu Leu Arg His Lys Leu Lys Tyr Val Pro His Glu Tyr Ile Glu Leu
            180                 185                 190

Ile Glu Ile Ala Arg Asn Ser Thr Gln Asp Arg Ile Leu Glu Met Lys
        195                 200                 205

Val Met Glu Phe Phe Met Lys Val Tyr Gly Tyr Arg Gly Lys His Leu
    210                 215                 220

Gly Gly Ser Arg Lys Pro Asp Gly Ala Ile Tyr Thr Val Gly Ser Pro
225                 230                 235                 240

Ile Asp Tyr Gly Val Ile Val Asp Thr Lys Ala Tyr Ser Gly Gly Tyr
                245                 250                 255

Asn Leu Pro Ile Gly Gln Ala Asp Glu Met Gln Arg Tyr Val Glu Glu
            260                 265                 270

Asn Gln Thr Arg Asn Lys His Ile Asn Pro Asn Glu Trp Trp Lys Val
        275                 280                 285

Tyr Pro Ser Ser Val Thr Glu Phe Lys Phe Leu Phe Val Ser Gly His
    290                 295                 300

Phe Lys Gly Asn Tyr Lys Ala Gln Leu Thr Arg Leu Asn His Ile Thr
305                 310                 315                 320

Asn Cys Asn Gly Ala Val Leu Ser Val Glu Glu Leu Leu Ile Gly Gly
                325                 330                 335

Glu Met Ile Lys Ala Gly Thr Leu Thr Leu Glu Glu Val Arg Arg Lys
            340                 345                 350

Phe Asn Asn Gly Glu Ile Asn Phe
        355                 360

```
<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Glu Ala Ala Ala Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Lys Ser Glu Ala Ala Ala Arg
1               5

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide

<400> SEQUENCE: 7

Glu Leu Glu Glu Lys Lys Ser Glu Leu Arg His Lys
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Glu Ala Ala Ala Arg
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa is any amino acid residue except proline or
      glycine

<400> SEQUENCE: 9

Glu Xaa Xaa Xaa Arg
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
```

```
<223> OTHER INFORMATION: Xaa is any amino acid residue except proline or
      glycine

<400> SEQUENCE: 10

Glu Xaa Xaa Xaa Lys
1               5

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide

<400> SEQUENCE: 11

Leu Arg Gly Ser Gln Leu Val Lys Ser Glu Leu Glu Glu Lys Lys Ser
1               5                   10                  15
```